United States Patent
Hurley et al.

(10) Patent No.: US 6,605,062 B1
(45) Date of Patent: Aug. 12, 2003

(54) CATHETER FOR GUIDEWIRE SUPPORT OR EXCHANGE

(75) Inventors: Bridget A. Hurley, San Francisco, CA (US); Jenny E. Tsien, San Jose, CA (US); David Chi, Santa Clara, CA (US); Gregg A. Jackson, San Francisco, CA (US); Steven James Bigus, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/389,159

(22) Filed: Sep. 2, 1999

(51) Int. Cl.[7] .............................................. A61M 5/178
(52) U.S. Cl. ................................................ 604/164.13
(58) Field of Search ....................... 604/164.01, 164.02, 604/164.1, 164.11, 164.13, 523, 264, 43, 95.01, 95.02, 165.01

(56) References Cited

U.S. PATENT DOCUMENTS

| | | | |
|---|---|---|---|
| 2,624,341 A | 1/1953 | Wallace | 128/350 |
| 3,835,863 A | 9/1974 | Goldberg et al. | 128/350 |
| 4,142,528 A | 3/1979 | Whelan, Jr. et al. | 128/350 |
| 4,467,790 A | 8/1984 | Schiff | 128/1 |
| 4,569,347 A | 2/1986 | Frisbie | 128/344 |
| 4,585,435 A | 4/1986 | Vaillancourt | 604/27 |
| 4,596,557 A | 6/1986 | Pexa | 604/86 |
| 4,616,652 A | 10/1986 | Simpson | 128/344 |
| 4,661,110 A | 4/1987 | Fortier et al. | 604/256 |
| 4,748,982 A | 6/1988 | Horzewski et al. | |
| 4,762,129 A | 8/1988 | Bonzel | 128/344 |
| 4,771,777 A | 9/1988 | Horzewski et al. | |
| 4,915,704 A | 4/1990 | Miyasaka et al. | 604/256 |
| 4,928,693 A | 5/1990 | Goodin et al. | 128/637 |
| 4,932,413 A | 6/1990 | Shockey et al. | 128/657 |
| 4,944,745 A | 7/1990 | Sogard et al. | 606/194 |
| 4,947,864 A | * 8/1990 | Shockey et al. | 128/772 |
| 4,988,356 A | 1/1991 | Crittenden et al. | |
| 5,053,003 A | 10/1991 | Dadson et al. | 604/28 |

(List continued on next page.)

FOREIGN PATENT DOCUMENTS

| | | |
|---|---|---|
| EP | 0-505686 A1 * | 9/1992 |
| WO | 93/05841 | 4/1993 |
| WO | 93/13827 | 7/1993 |
| WO | 96/04035 | 2/1996 |

OTHER PUBLICATIONS

Cook Cardiology–Wire Guide Exchange Set, 1993.
Monorail–GEX Guidewire Exchange Catheter. Taken from the Schneider GEX Brochure, Monorail.

*Primary Examiner*—Brian L. Casler
*Assistant Examiner*—Ann Y. Lam
(74) *Attorney, Agent, or Firm*—Fulwider Patton Lee & Utecht, LLP

(57) ABSTRACT

A catheter and method of using same for support or exchange of a guidewire during a percutaneous procedure which has at least one lumen in an elongate shaft with a proximal port and a distal port in fluid communication via an inner lumen. The catheter has a longitudinal slit in the inner lumen beginning at the proximal end of the elongate shaft and extends distally. An elongate support member is secured to the elongate shaft to provide axial rigidity to the catheter. Optionally, a second inner lumen is disposed within the elongate shaft adjacent the aforementioned inner lumen which has an intermediate port disposed distally of the proximal end of the elongate shaft.

25 Claims, 5 Drawing Sheets

U.S. PATENT DOCUMENTS

| | | |
|---|---|---|
| 5,129,887 A | 7/1992 | Euteneuer et al. ............ 606/194 |
| 5,135,535 A | 8/1992 | Kramer |
| 5,171,222 A | 12/1992 | Euteneuer et al. |
| 5,183,471 A | 2/1993 | Wilk ............................ 604/284 |
| 5,213,575 A | 5/1993 | Scotti ............................ 604/95 |
| 5,250,073 A * | 10/1993 | Cottone, Jr. .................. 606/206 |
| 5,281,203 A | 1/1994 | Ressemann .................. 604/164 |
| 5,328,472 A | 7/1994 | Steinke et al. ............... 604/102 |
| 5,389,087 A * | 2/1995 | Miraki ......................... 604/247 |
| 5,391,146 A | 2/1995 | That et al. ..................... 604/95 |
| 5,395,335 A | 3/1995 | Jang |
| 5,415,639 A | 5/1995 | VandenEinde et al. ....... 604/283 |
| 5,437,288 A | 8/1995 | Schwartz et al. ............ 128/772 |
| 5,449,362 A | 9/1995 | Chaisson et al. ............ 606/108 |
| 5,496,346 A | 3/1996 | Horzewski et al. |
| 5,531,700 A | 7/1996 | Moore et al. ................ 604/164 |
| 5,540,236 A | 7/1996 | Ginn ............................ 128/772 |
| 5,554,118 A * | 9/1996 | Jang ............................... 604/96 |
| 5,571,094 A | 11/1996 | Sirhan .......................... 604/284 |
| 5,626,600 A | 5/1997 | Horzewski et al. |
| 5,709,658 A | 1/1998 | Sirhan |
| 5,720,300 A * | 2/1998 | Fagan et al. ................. 128/772 |
| 5,772,642 A * | 6/1998 | Ciamacco, Jr. et al. ...... 604/280 |
| 5,891,056 A | 4/1999 | Ramzipoor .................. 600/585 |
| 5,980,484 A * | 11/1999 | Ressemann et al. |
| 5,997,497 A * | 12/1999 | Nita et al. ..................... 604/22 |
| 6,013,069 A | 1/2000 | Sirhan et al. ................ 604/524 |
| 6,129,701 A * | 10/2000 | Cimino ......................... 604/35 |
| 6,273,899 B1 | 8/2001 | Kramer |

* cited by examiner

CATHETER FOR GUIDEWIRE SUPPORT OR EXCHANGE

BACKGROUND

This invention generally relates to intravascular procedures, such as percutaneous transluminal coronary angioplasty (PTCA), and particularly to the exchange or support of guidewires during such procedures.

In typical PTCA procedures, a guiding catheter is positioned within a patient's vasculature such that the distal end of the guiding catheter is disposed within the ostium. A guidewire is advanced through the guiding catheter and into the patient's coronary arteries. The guidewire is maneuvered by advancing and rotating the distal tip which normally has an asymmetric "J" shape imposed on it to enable selection of various branches of the coronary vasculature. Once the guidewire is positioned in a desired location, a dilatation catheter is advanced over the guidewire into the patient's coronary artery until the balloon on the distal extremity of the dilatation catheter is properly positioned across the lesion to be dilated. Once properly positioned across the lesion, the flexible,/relatively inelastic balloon on the dilatation catheter is inflated to a predetermined size with radiopaque liquid at relatively high pressures (e.g., generally 4–20 atmospheres or more) to dilate the stenosed region of the diseased artery. One or more inflations of the balloon may be required to complete the dilatation of the stenosis. After the last dilatation, the balloon is deflated so that the dilatation catheter can be removed from the dilated stenosis and blood flow can resume through the dilated artery.

One difficulty that can be encountered in the procedure above is the inability to cross the lesion or stenosis with the distal end of the guidewire. This can be due to a variety of circumstances, including, a tight stenotic lesion with insufficient lumen patency to allow passage of a guidewire. Also, the lesion may be completely blocked as is found with a chronic total occlusion (CTO) and the guidewire may require axial support at the distal end in order to cross such a CTO. It is also possible that a guidewire may not be suitably configured to cross a given lesion or stenosis. In such a case, there is a need to replace an in-place guidewire with another guidewire having a different structure, e.g. from a floppy-type design with a separate shaping ribbon to an intermediate or standard with a core wire which extends to the distal tip of the guidewire. The need to withdraw an in-place guidewire also occurs when the distal tip of the in-place guidewire needs to be reshaped to change the angle of attack to a branch coronary artery. Because of this, it is desirable for the physician to be able to exchange guidewires and support a pre-positioned guidewire to facilitate crossing of a difficult lesion.

In addition, a significant improvement in dilatation catheters has been the introduction of rapid exchange type dilatation catheters. These catheters have a short guidewire receiving sleeve or inner lumen extending through the distal portion of the catheter which extend from a distal guidewire port in the distal end of the catheter to a proximal guidewire port spaced proximal to the proximal end of the dilatation balloon. The proximal guidewire port is usually located at least about 10 cm and usually not more than about 50 cm from the distal guidewire port. A slit is some times provided in the catheter wall in fluid communication with the guidewire receiving inner lumen which extends from the second guidewire port, preferably to a location proximal to the proximal end of the inflatable balloon to aid in the removal of the catheter from a guidewire upon withdrawal of the catheter from the patient. The structure of the catheter allows for the rapid exchange of the catheter without the need for the use of an exchange wire or adding a guidewire extension to the proximal end of the guidewire.

Rapid exchange type dilatation catheters are described and claimed in U.S. Pat. No. 5,040,548 (Yock), U.S. Pat. No. 5,061,273 (Yock), U.S. Pat. No. 5,300,085 (Yock), U.S. Pat. No. 5,350,395 (Yock), U.S. Pat. No. 4,748,982 (Horzewski et al.), U.S. Pat. No. 5,154,725 (Leopold) and U.S. Pat. No. 5,346,505 (Leopold) which are incorporated herein in their entirety by reference.

However, one significant inconvenience with the use of rapid exchange type dilatation catheter systems is the inability to remove a guidewire already in place within a patient's vasculature during an angioplasty procedure without losing access to the vascular location. There has been no convenient way in-which a replacement guidewire might be advanced through the vasculature and into the short guidewire receiving inner lumen in the distal extremity of a rapid exchange type dilatation catheter.

What has been needed is a convenient means to withdraw an in-place guidewire from a rapid exchange type dilatation catheter and either replace the in-place guidewire with another guidewire or to reposition the inplace guidewire within the rapid exchange type dilatation catheter.

SUMMARY

The invention is directed generally to an elongate intracorporeal device for facilitating access for diagnostic devices, therapeutic devices, or the like which are advanced over a guidewire within a patient's body. Specifically, the invention is directed to a catheter for support or exchange of a guidewire. An embodiment of a catheter with features of the invention has an elongate shaft with an inner lumen within shaft. The elongate shaft has a proximal end and a distal end with a proximal port of the inner lumen at the proximal end of the shaft and a distal port of the inner lumen at the distal end of the shaft. There is an intermediate port on the elongate shaft in fluid communication with the inner lumen disposed between the proximal port and the distal port. An optional longitudinal slit in an outer wall of the elongate shaft extends distally from the proximal port of the inner lumen at the proximal end of the elongate shaft. A longitudinal support member is secured to the elongate shaft in order to provide axial support to the catheter.

The distance from the distal end of the elongate shaft to the intermediate port can be about 15 to about 45 cm, specifically about 30 to about 40 cm. This allows the catheter to be loaded over a proximal end of a first guidewire with the distal end of the guidewire positioned within a patient's body. In use, the proximal end of the first guidewire is backloaded into the distal port of the inner lumen of the elongate shaft and exits through the intermediate port. An exit tube can be disposed within the intermediate port to facilitate discharge of the proximal end of the guidewire from the intermediate port during the backloading process. The catheter can thus be loaded over the first guidewire and advanced distally over the first guidewire while leaving the distal end of the first guidewire positioned within the patient's body. Once the catheter has been advanced distally to a desired position, the first guidewire may be withdrawn from the patient and a second guidewire front loaded into the proximal port of the inner lumen and advanced distally into the patient into the position that the first guidewire occupied prior to being withdrawn. Again, the second guidewire can be withdrawn from the patient and a third guidewire can be frontloaded into the proximal port, and so on. The proximal end of the elongate shaft of the catheter may then be pulled laterally with respect to the second guidewire such that a corresponding proximal end of the second guidewire emerges laterally from the longitudinal slit. The catheter can thereafter be withdrawn proximally while holding the proximal end of the second guidewire in fixed axial position, and peeling the catheter off of the second guidewire while the catheter is being retracted.

The process can then be repeated if it is desired to replace the second guidewire with a new third guidewire, and so on. In this way, the physician can exchange guidewires while maintaining access to a desired position within a patient's body. In addition, the distal end of the elongate shaft can be advanced distally over a guidewire to a position which enables the distal end of the elongate shaft to provide axial support and pushability to the distal end of the guidewire. This can be used to facilitate advancement of the distal end of a guidewire across a tight stenosis, chronic total occlusion or the like.

In another embodiment of a catheter having features of the invention an elongate shaft of the catheter has a proximal end, a distal end, a first inner lumen and a second inner lumen, with both inner lumens being suitable for passage of a desired guidewire. The first inner lumen has a distal port at the distal end of the elongate shaft and an intermediate port at a position proximal of the distal end of the elongate shaft and distal of the proximal end of the elongate shaft. The second inner lumen has a distal port at the distal end of the shaft and a proximal port at the proximal end of the shaft. There is optionally a longitudinal slit in a wall of the elongate shaft, which is in fluid communication with the second inner lumen and which extends distally from the proximal port of the second inner lumen. A longitudinal support member is secured to the elongate shaft for axial support of the exchange catheter.

These and other advantages of the invention will become more apparent from the following detailed description of the invention when taken in conjunction with the accompanying exemplary drawings.

DETAILED DESCRIPTION

Figure 1:
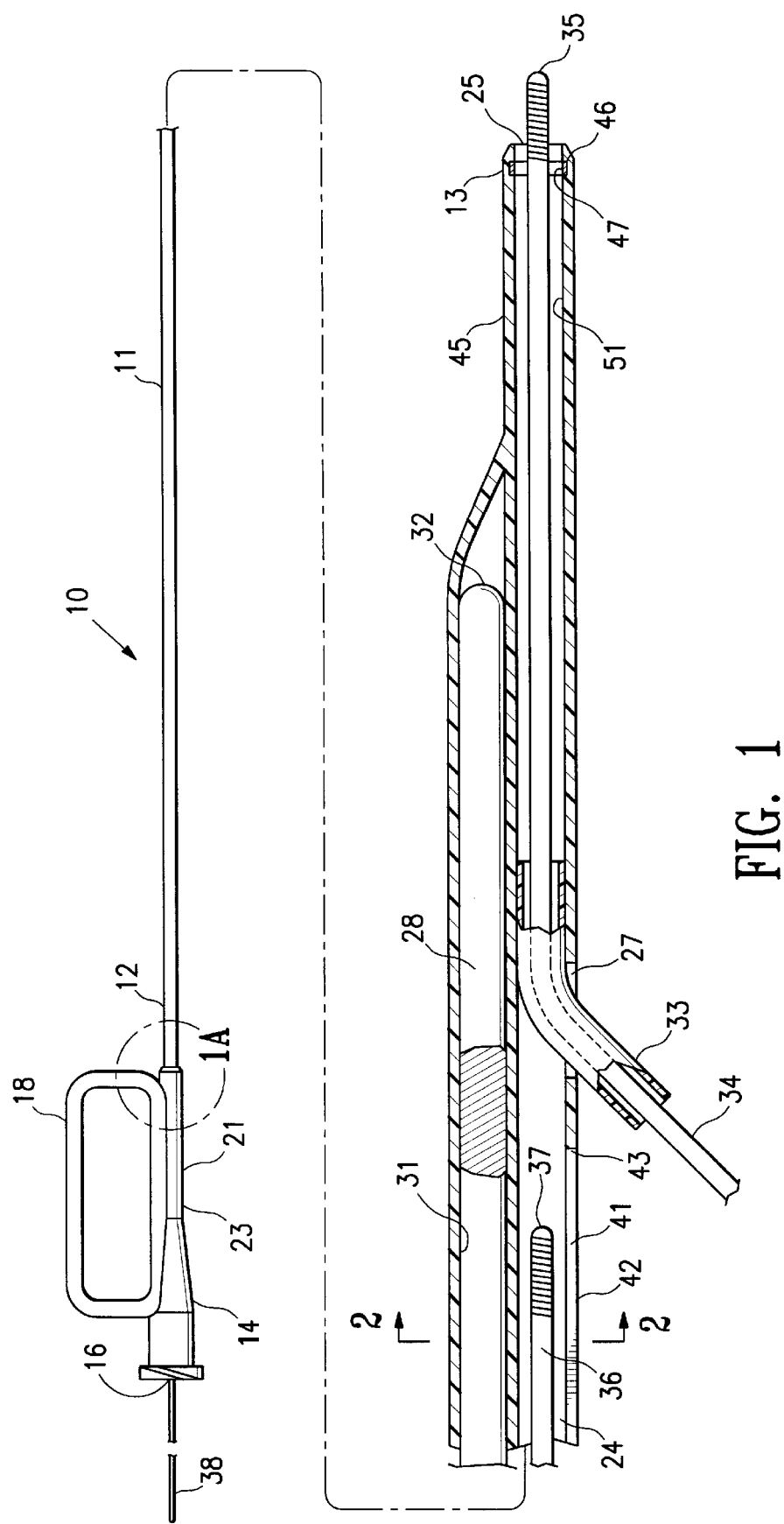
FIG. 1 shows an elevational view in partial longitudinal section of a catheter having features of the invention.
Figure 2:
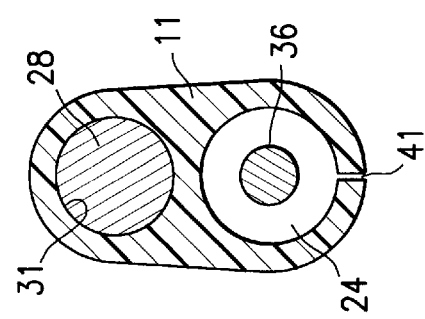
FIG. 2 is a transverse cross sectional view of the catheter of FIG. 1 taken along lines 2—2 of FIG. 1.
Figure 1A:
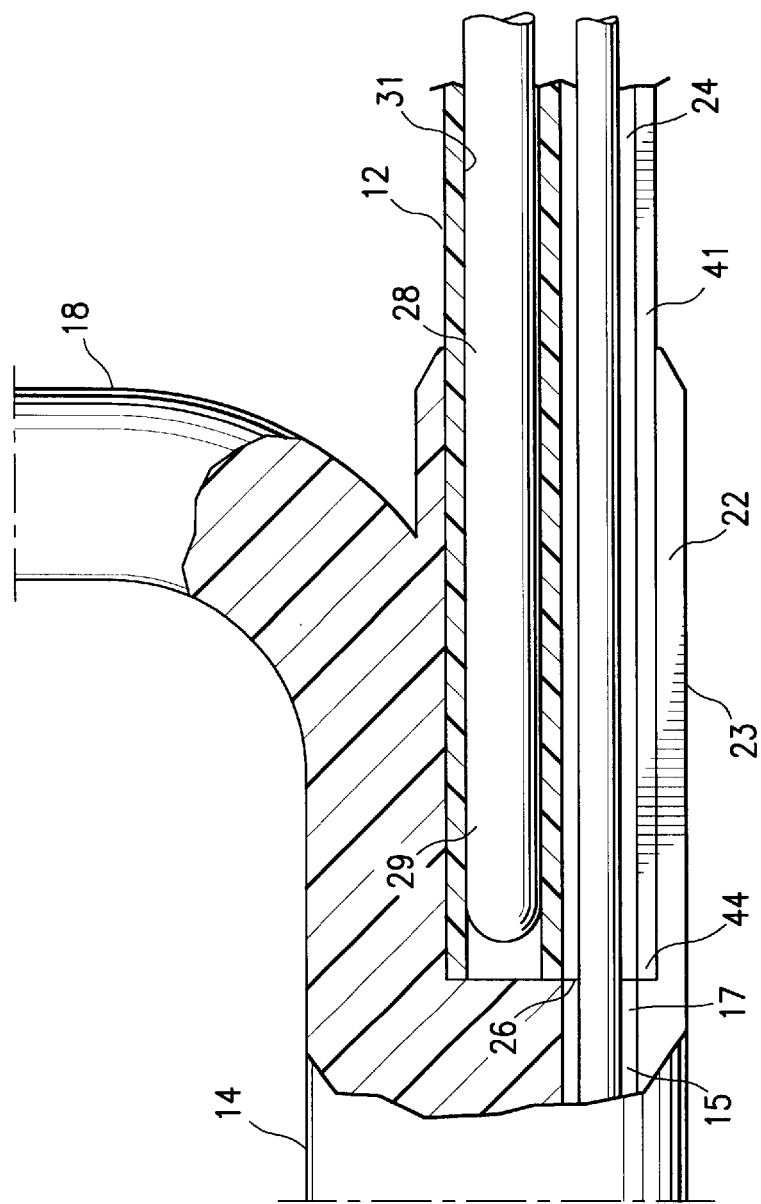
FIG. 1A is an enlarged view in partial section of the portion of the catheter in FIG. 1 designated by circle 1A.

FIGS. 1–2 illustrates an embodiment of a catheter 10 having features of the invention. An elongate shaft 11 has a proximal end 12 and a distal end 13. A side arm 14 is disposed on the proximal end 12 of the elongate shaft 11 and is adapted to accept a variety of male luer fittings for hemostasis, fluid delivery and the like. A side arm lumen 15 having a proximal end 16 and a distal end 17 is disposed within the side arm 14 and extends longitudinally therein. A side arm handle 18 is secured to the side arm 14 to provide a physician using the catheter 10 a site for grasping a proximal end 21 of the catheter 10 and applying force in a lateral direction with respect to the longitudinal axis of the side arm 14 elongate shaft 11.

The side arm 14 has a slit 22 from an outside surface 23 of the side arm 14 to the side arm lumen 15, however the slit 22 may also be configured to penetrate only partially through the side arm 14. The slit 22 can be disposed in the side arm 14 on the side of the side arm 14 opposite the side arm handle 18. An inner lumen 24 extends longitudinally within the elongate shaft 11 and has a distal port 25 at the distal end 13 of the elongate shaft 11 and a proximal port 26 at the proximal end 12 of the elongate shaft 11. The proximal port 26 is disposed adjacent with the distal end 17 of the side arm lumen 15 such that the inner lumen 24 of the elongate shaft 11 is in fluid communication with the side arm lumen 15 of the side arm 14. An intermediate port 27 in fluid communication with the inner lumen 24 is disposed proximal of the distal end 13 of the elongate shaft 11 and distal of the proximal end 12 of the elongate shaft 11. The distance between the distal end 13 of the elongate shaft 11 and the intermediate port 27 should be short enough to allow rapid exchange and removal of the catheter 10 at a proximal end of a guidewire and long enough such that the intermediate port 27 remains within a lumen of a guiding catheter during use. The distance from the distal end 13 of the elongate shaft 11 to the intermediate port 27 can be from about 5 to about 45 cm, specifically about 30 to about 40 cm. The elongate shaft 11 can be made from a polymer of a blend of high density and low density polyethylene. The elongate shaft 11 can also be made from polyurethane, PVC, high density polyethylene, low density polyethylene, flouropolymers or the like or any blend thereof.

A transverse dimension or diameter of the inner lumen 24 of the elongate shaft 11 is configured to accept commercially available guidewires having outer diameters from about 0.01 to about 0.02 inches for coronary guidewires and from about 0.03 to about 0.05 inches for guidewires used in the periphery. Typically, the transverse dimension of the inner lumen 24 of the elongate shaft 11 will be substantially constant along the longitudinal length of the lumen and will be about 0.014 to about 0.018 inches. The transverse dimension of the inner lumen 24 may also taper slightly to a reduced dimension distally at the distal end of lumen 24 in order to achieve a close fit with a desired size of guidewire. The distal end 13 of the elongate shaft 11 is optionally configured to engage a rapid exchange port of a rapid exchange dilatation or stent delivery catheter. An outer diameter of the distal end 13 of the elongate shaft 11 can be from about 0.01 to about 0.04 inch, specifically about 0.018 to about 0.02 inch.

Figure 6:
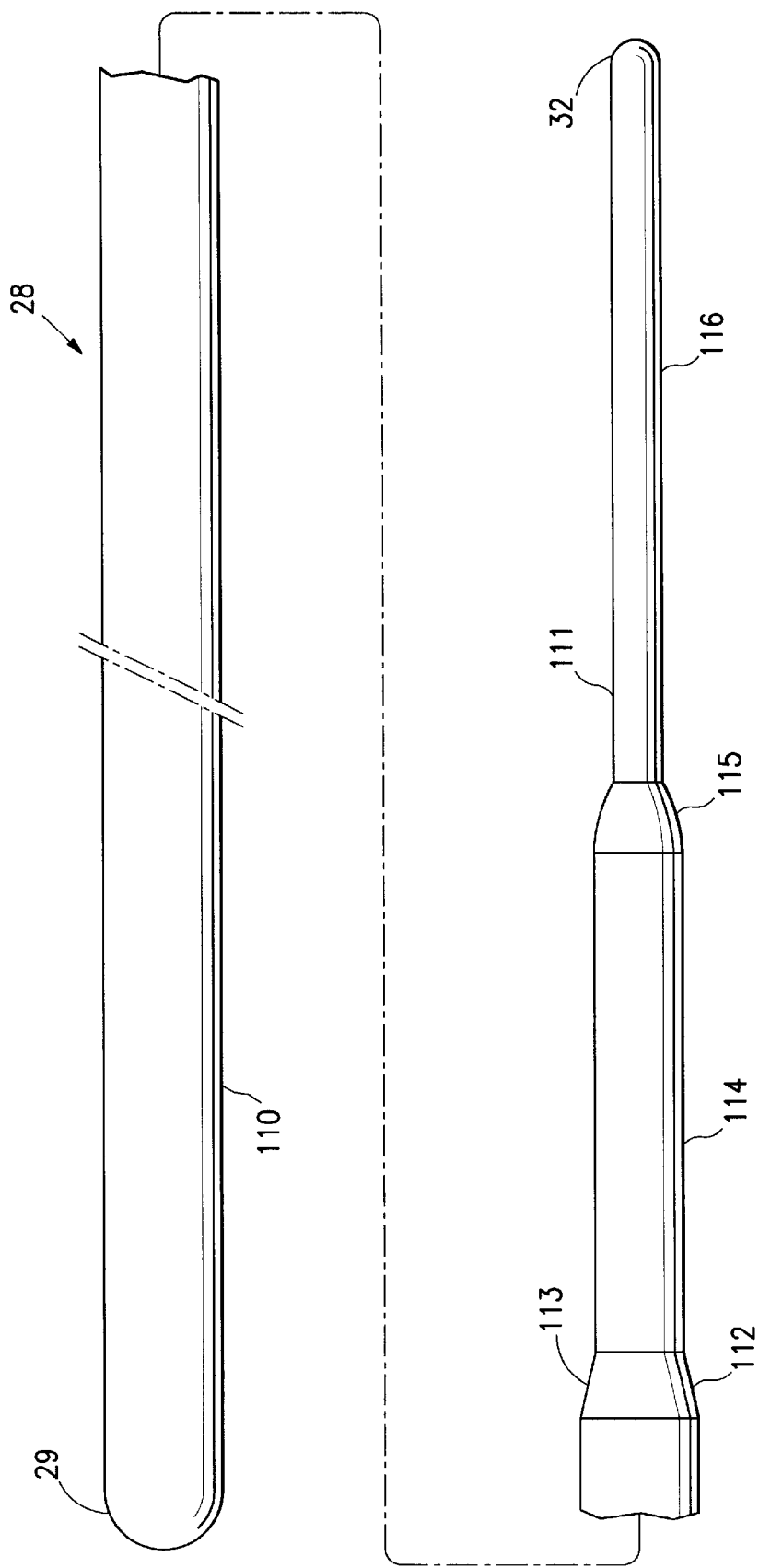
FIG. 6 is an elevational view of an elongate longitudinal support member having features of the invention.

A longitudinal support member 28, shown in greater detail in FIG. 6, has a proximal end 29 and is disposed within a longitudinal support member lumen 31 of the elongate shaft 11 generally parallel to the inner lumen 24 which is adjacent thereto. A distal end 32 of the longitudinal support member 28 is disposed proximal of the distal end 13 of the elongate shaft 11. The distal end 32 of the longitudinal support member 28 is typically about 2 to about 20 cm proximal of the distal end 13 of the elongate shaft 11, specifically about 3 to about 7 cm proximal of the distal end 13 of the elongate shaft 11.

An exit tube 33 is removably disposed in the inner lumen 24 and extends from the intermediate port 27 so as to direct or eject a proximal end (not shown) of a first guidewire 34 out of the intermediate port 27 upon backloading of the first guidewire 34 into the inner lumen 24 of the elongate shaft 11. Once the proximal end of the first guidewire is ejected from the intermediate port 27, the exit tube 33 can be removed from the intermediate port by pulling it out and sliding it proximally off the first guidewire 34. A distal end 35 of the first guidewire 34 is disposed extending slightly from the distal port 25 of the inner lumen 24. The exit tube 33 is can be made from polyimide, but can also be made from a variety of other materials including nylon, PE, polyurethane, delrin, PET or a metal. An inside transverse dimension of the exit tube 33 should allow passage of a guidewire of a desired outer diameter, while allowing for an outer transverse dimension that allows passage within the inner lumen 24 of the elongate shaft 11. The outer transverse dimension of the exit tube 33 can be from about 0.016 to about 0.025 for use with coronary guidewires and about 0.038 to about 0.045 for use with peripheral guidewires. An inner transverse dimension of the exit tube 33 can be from about 0.012 to about 0.020 inch, specifically about 0.015 to about 0.017 inch, for use with coronary guidewires.

A second guidewire 36 is shown disposed within the inner lumen 24 of the elongate shaft 11 with a distal end 37 of the second guidewire 36 disposed proximal of the intermediate port 27. An optional longitudinal slit 41 is disposed in an outer wall 42 of the inner lumen 24 and can extend from the proximal port 26 of the inner lumen 24 at the proximal end 12 of the elongate shaft 11 to a position proximal of the intermediate port 27. The longitudinal slit 41 can, however, extend any suitable distance distally from the proximal port 26 to the distal port 25 of the inner lumen 24. The longitudinal slit 41 can be configured to penetrate completely or partially through the outer wall 42 of the inner lumen 24. The distal extremity 43 of the longitudinal slit 41 should be sufficiently close to the distal end 13 of the elongate shaft 11 so that the catheter 10 can be peeled off the proximal end of a guidewire of non-exchange wire length without axially displacing the guidewire. Typically, the distance from a distal extremity 43 of the longitudinal slit 41 to the distal end 13 of the elongate shaft 11 is about 30 to about 50 cm. A proximal end 44 of the longitudinal slit 41 is aligned with the slit 22 of the side arm 14 so that a proximal end of a guidewire can be pulled laterally through the slit 22 of the sidearm 14 and the longitudinal slit 41 of the elongate shaft 11 while the catheter 10 is being removed from the guidewire. The side arm 14 can be molded over the proximal end 12 of the elongate shaft 11 allowing for the slit 22 of the side arm 14 and longitudinal slit 41 of the elongate shaft 11 to be cut at the same time by a suitable cutting method, such as a razor blade.

The distal end 35 of the first guidewire 34 is shown in FIG. 1 as fitting loosely in the inner lumen 24 and distal port 25 of the inner lumen 24 for the purposes of clarity of illustration. Preferably, an outer transverse dimension or diameter of the distal end 35 of the first guidewire 34 would be close fitting with an inner transverse dimension or diameter of the distal port 25 and inner lumen 24 of the distal end 13 of the elongate shaft 11. Typically, there is about 0.001 to about 0.004 inch of clearance between the first guidewire 34 and an inner transverse dimension of the distal port 25. This close fit should provide for a desirable low profile for a distal end 45 of the catheter but allows for axial translation of a guidewire disposed within the inner lumen 24 which facilitates advancement of the catheter 10 and guidewire across tight stenosis or chronic total occlusions.

A radiopaque marker 46 is shown disposed within the inner lumen 24 at the distal end 13 of the elongate shaft 11 for visualization of the position of the catheter 10 under flouroscopic imaging or the like. An inside surface 47 of the radiopaque marker 46 can be flush with an adjacent inside surface 51 of the inner lumen 24 to create a smooth transition between the inside surfaces which allows a guidewire or other intracorporeal device to be passed through the inner lumen 24 past the radiopaque marker 46 without catching or snagging on an edge of the radiopaque marker 46. The axial length of the radiopaque marker 46 can be from about 0.5 to about 3.0 mm, specifically about 1 to about 2 mm. The radiopaque marker 46 can be made from any suitable radiopaque material or materials including gold, platinum, tantalum, tungsten, platinum-iridium and the like. The wall thickness of the radiopaque marker 46 can be about 0.0005 to about 0.002 inch, specifically about 0.001 to about 0.002 inch.

In use, the proximal end (not shown) of the first guidewire 34 is backloaded into the distal port 25 of the inner lumen 24 of the elongate shaft 11 and exits through the intermediate port 27. The exit tube 33 can be disposed within the intermediate port to facilitate discharge of the proximal end of the first guidewire 34 from the intermediate port 27 during the backloading process. The exchange catheter 10 can thus be loaded over the first guidewire 34 and advanced distally over the first guidewire 34 while leaving the distal end 35 of the first guidewire 34 positioned within the patient's body. Once the exchange catheter 10 has been advanced distally to a desired position and optionally used for guidewire support, the first guidewire 34 may be withdrawn from the patient and the second guidewire 36 front loaded into the proximal port 26 of the inner lumen 24 and advanced distally into the patient into the position that the first guidewire 34 occupied prior to being withdrawn. Additional guidewires may be exchanged thereafter. The proximal end 12 of the elongate shaft 11 of the exchange catheter 10 may then be pulled laterally with respect to the second guidewire 36 such that a corresponding proximal end 38 of the second guidewire 36 emerges laterally from the longitudinal slit 41. The catheter 10 can thereafter be withdrawn proximally while holding the proximal end 38 of the second guidewire 36 in fixed axial position, and peeling the catheter 10 off of the second guidewire 36 while the catheter 10 is being retracted.

Figure 3:
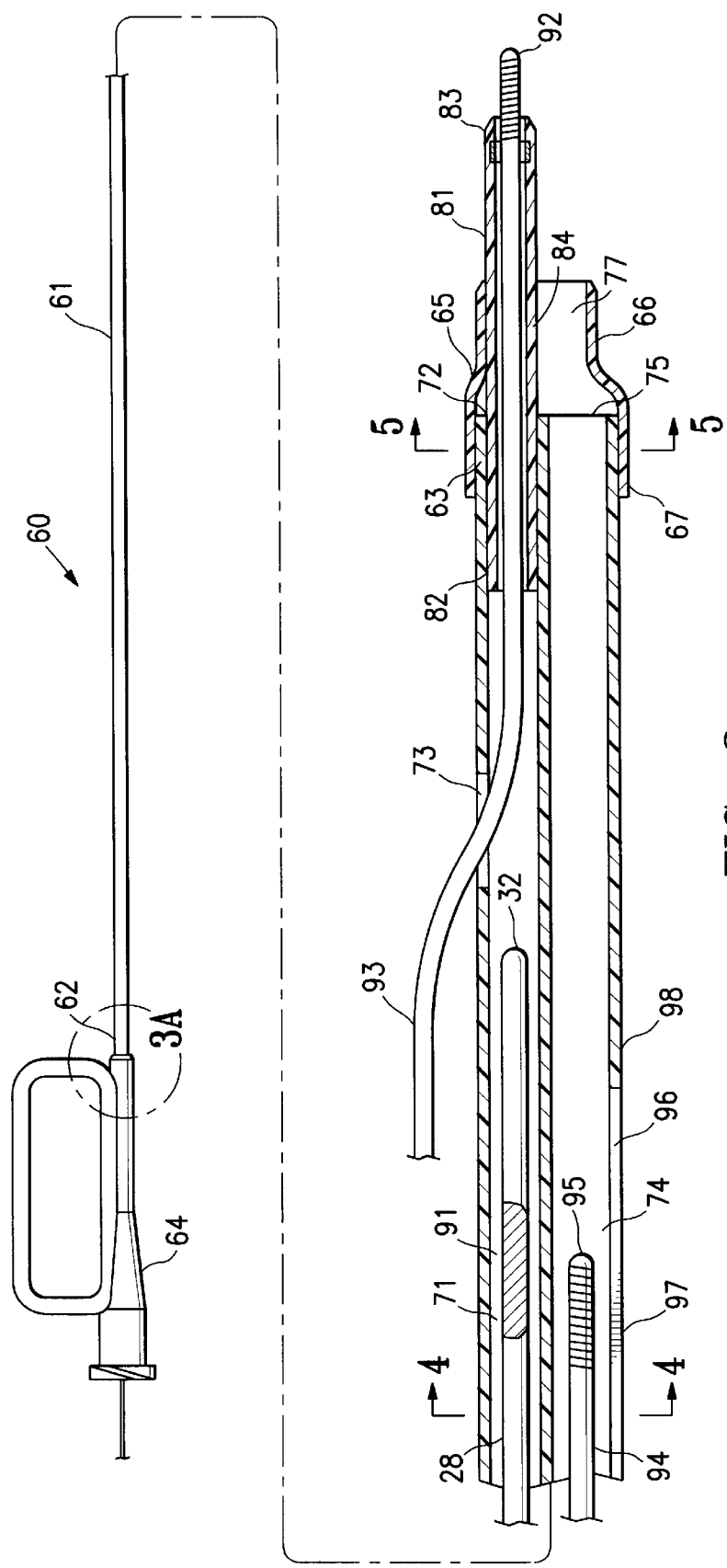
FIG. 3 is an elevational view in partial longitudinal section of an alternative embodiment of a catheter having features of the invention.
Figure 4:
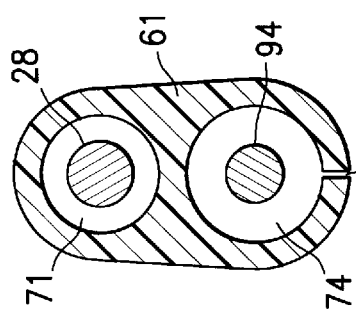
FIG. 4 is a transverse cross sectional view of the catheter of FIG. 3 taken along lines 4—4 of FIG. 3.
Figure 5:
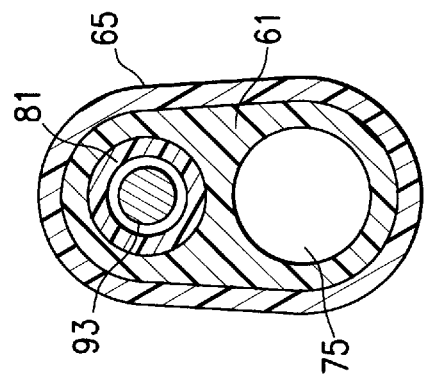
FIG. 5 is a transverse cross sectional view of the catheter of FIG. 3 taken along lines 5—5 of FIG. 3.
Figure 3A:
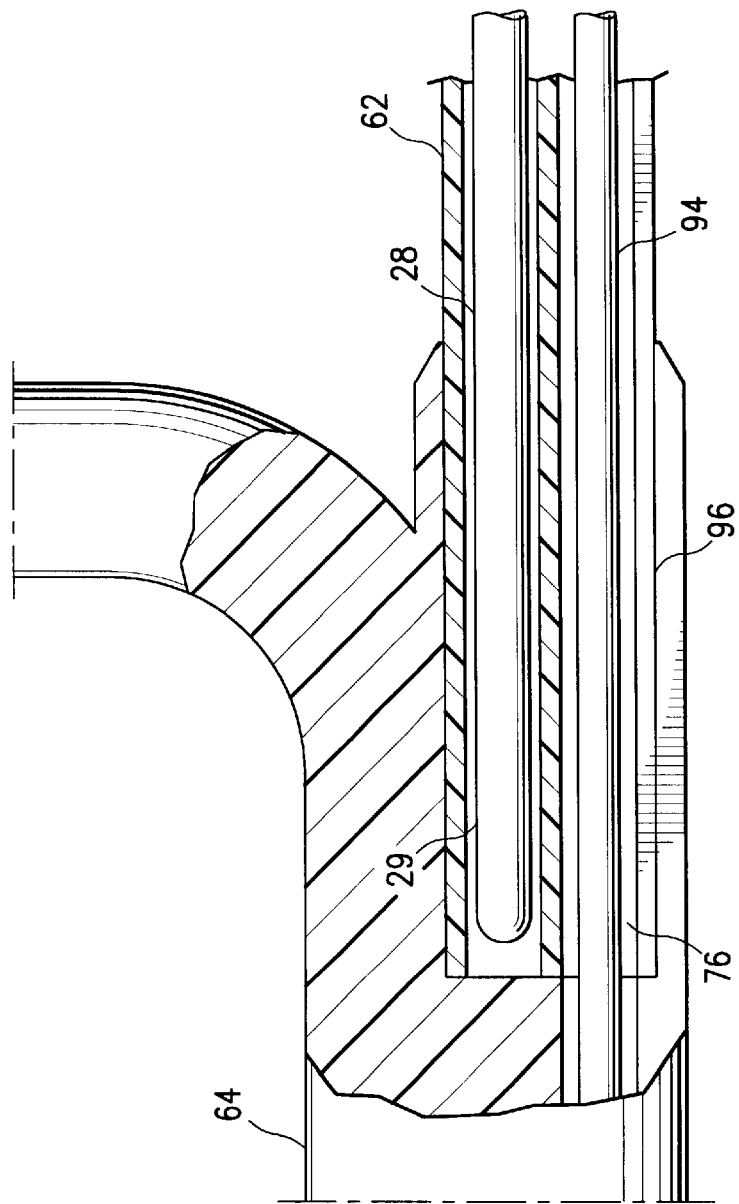
FIG. 3A is an enlarged view of the portion of the catheter of FIG. 3 designated by the circle 3A.

FIGS. 3–5 illustrate another embodiment of a catheter 60 for exchange or support of a guidewire having features of the invention. An elongate shaft 61 has a proximal end 62 and a distal end 63. A side arm 64 is disposed on the proximal end 62 of the elongate shaft 61 and is adapted to accept a variety of male luer fittings for hemostasis. A distal bumper member 65 which can be made from heat shrinkable tubing is disposed about and secured to the distal end 63 of the elongate shaft 61 which has a distal section 66 with a smaller transverse dimension than a transverse dimension of a proximal section 67 of the bumper member 65. A first inner lumen 71 is disposed within the elongate shaft 61 and has a distal port 72 at a distal end 63 of the shaft 61 and an intermediate port 73 at a position that is proximal of the distal end 63 of the elongate shaft 61 and distal of the proximal end 62 of the elongate shaft 61. The intermediate port 73 of the first inner lumen 71 can be disposed about 25 to about 45 cm from the distal end 63 of the elongate shaft 61, specifically about 30 to about 40 cm from the distal end 63 of the elongate shaft 61. A second inner lumen 74 extends within the elongate shaft 61 adjacent the first inner lumen 71 and has a distal port 75 at the distal end 63 of the elongate shaft 61 and a proximal port 76 at the proximal end 62 of the elongate shaft 61.

The distal bumper member 65 has a lumen 77 which is in fluid communication with the first inner lumen 71 and second inner lumen 74 of the elongate shaft 61. A tubular tip member 81 having a proximal end 82 and a distal end 83 is disposed at the distal end 63 of the elongate shaft 61 with the proximal end 82 of the tubular tip member 81 within the first inner lumen 71 of the elongate shaft 61. An intermediate portion 84 of the tubular tip member 81 is disposed within the lumen 77 of the distal bumper member 65, and the distal end 83 of the tubular tip member 81 extends distally from the distal section 66 of the distal bumper member 65. The elongate shaft 61 is preferably made from a polymer of a blend of high density and low density polyethylene. The elongate shaft 61 can also be made from polyurethane, PVC, high density polyethylene, low density polyethylene, flouropolymers or the like.

Longitudinal support member 28, shown in more detail in FIG. 6, has a proximal end 29 and a distal end 32 and is disposed within a longitudinal support member lumen 91 of the elongate shaft 61. The longitudinal support member lumen 91 is preferably an extension of the first inner lumen 71 extending proximally from the port 73. The distal end 32 of the longitudinal support member 28 is typically about 2 to about 20 cm proximal of the distal end 63 of the elongate shaft 61, preferably about 3 to about 7 cm proximal of the distal end 63 of the elongate shaft 61.

A distal end 92 of a first guidewire 93 is disposed extending slightly from the distal port 72 of the first inner lumen 71. A second guidewire 94 is shown disposed within the second inner lumen 74 of the elongate shaft 61 with a distal end 95 of the second guidewire 94 disposed proximally of the distal port 75 of the second inner lumen 74. A longitudinal slit 96 is optionally disposed in an outer wall 97 of the elongate shaft 61 and can be configured to extend partially or completely through the outer wall 97. If the longitudinal slit 96 is configured to extend only partially through the outer wall 97, contrast medium or the like can still be injected through the second inner lumen 74 without leakage through the longitudinal slit 96. The longitudinal slit 97 is in fluid communication with the second inner lumen 74 and extends distally from the proximal port 76 of the second inner lumen 74 at the proximal end 62 of the elongate shaft 61. The distance from the distal end 63 of the elongate shaft 61 to a distal extremity 98 of the longitudinal slit 96 can be about 20 to about 40 cm. The longitudinal slit 96 can, however, extend any suitable distance distally from the proximal port 76 of the second inner lumen 74 so as to allow for peeling the catheter 60 off the proximal portion of the second guidewire 94 disposed within a patient's body without the necessity of removing or axially displacing the guidewire 94.

In use, a proximal end of the first guidewire 93 positioned within a patient is backloaded into the distal port 72 of the first inner lumen 71 and exits the intermediate port 73 of the first inner lumen 71. An exit tube which is similar to exit tube 33 in FIG. 1 may be disposed within the proximal port 73 of the first inner lumen 71 to facilitate exiting of the proximal end of the first guidewire during backloading. The catheter 60 is then distally advanced over the first guidewire 93 to a desired position and optionally used for guidewire support. The second guidewire 94 may then be front loaded into the second inner lumen 74 and advanced to the desired site within the patient's body. Thus, this embodiment allows the physician to have two guidewires crossing the same lesion at the same time which assures guidewire position within the patient and eliminates the risk of having a lesion close off due to muscle spasm or the like, without a guidewire in place. Such a closing off of a lesion can lead to a need for emergency surgical intervention if a guidewire can not recross the closed off lesion. In addition, this feature can maintain and secure guidewire position during exchange and allows two guidewires of different stiffnesses to be used simultaneously and advanced independently in order to access and cross a lesion in a patient's artery. The first guidewire 93 may then be withdrawn once the second guidewire 94 is in place. Thereafter, the catheter 60 may be withdrawn by retracting the catheter and peeling it off the second guidewire through the longitudinal slit 96 simultaneously.

FIG. 6 illustrates an embodiment of a longitudinal support member 28 having features of the invention. The longitudinal support member 28 can provide catheter 10 of FIGS. 1–2 and catheter 60 of FIGS. 3–5 with axial support and pushability while controlling the amount of stiffness at the distal ends of the catheters. The longitudinal support member 28 has a proximal end 29, a distal end 32, a proximal section 110 and a distal section 111. The length of the proximal section 110 can be from about 50 to about 150 cm, specifically about 80 to about 130 cm. The proximal section 110 has a substantially constant diameter which can be from about 0.014 to about 0.02 inch, specifically about 0.016 to about 0.017 inch. The distal section 111 has a first distally tapering segment 112 at a proximal end 113 of the distal section 111 which can have a length up to about 10 cm, specifically about 1 to about 5 cm, and more specifically about 2 to about 3 cm. A first constant diameter segment 114 is disposed distally contiguous to the first distally tapering segment 112 and has an outer diameter of about 0.011 to about 0.015 inch, specifically about 0.012 to about 0.014 inch. A second distally tapering segment 115 is disposed distally contiguous to the first constant diameter segment 114 which can have a length up to about 10 cm, specifically about 1 to about 5 cm, and more specifically about 2 to about 3 cm. A second constant diameter segment 116 is disposed distally contiguous with the second distally tapering segment 115 and can have an outer diameter of about 0.002 to about 0.01 inch, specifically about 0.004 to about 0.009 inch, and more specifically about 0.006 to about 0.008 inch. The longitudinal support member 28 is preferably constructed from 316 or 304v stainless steel, but can also be made from NiTi, MP35N, L605, high tensile stainless steel, precipitation hardenable stainless steel or Elgiloy alloys thereof or the like.

While particular forms of the invention have been illustrated and described, it will be apparent that various modifications can be made without departing from the spirit and scope of the invention. Accordingly, it is not intended that the invention be limited, except as by the appended claims.

What is claimed is:

1. A guidewire exchange catheter comprising:
   an elongate shaft having
   a) a proximal end;
   b) a low profile distal end;
   c) an inner lumen extending therein from a proximal port at the proximal end to a distal port at the distal end;
   d) an intermediate port disposed between the proximal and distal port, which is in fluid communication with the inner lumen and which is a short distance away from the low profile distal end of the shaft;
   e) a longitudinal slit in an outer wall of the inner lumen extending distally from the proximal end;
   f) a sidearm disposed on the proximal end of the elongated shaft having a side arm lumen extending longitudinally therein in fluid communication with the inner lumen of the elongate shaft and having a slit that is aligned with the longitudinal slit of the elongate shaft and g) a longitudinal support member secured to the elongate shaft.

2. The catheter of claim 1 wherein a distal extremity of the longitudinal slit is about 30 to about 50 cm proximal of the distal end of the elongate shaft.

3. The catheter of claim 1 wherein the distance from the distal end of the elongate shaft to the intermediate port is about 25 to about 45 cm.

4. The catheter of claim 1 wherein the distance from the distal end of the elongate shaft to the intermediate port is about 30 to about 40 cm.

5. The catheter of claim 1 wherein the longitudinal support member further comprises a proximal section and a distal section and the distal section has at least one distally tapering segment which tapers distally to a reduced transverse cross section.

6. The catheter of claim 5 wherein the distal section of the longitudinal support member comprises a first distally tapering segment disposed proximal to a second distally tapering segment and a first constant diameter segment axially disposed between the two distally tapering segments and a second constant diameter segment disposed axially distal of the second distally tapering segment.

7. The catheter of claim 1 wherein the longitudinal support member comprises a material selected from the group consisting of stainless steel, NiTi, MP35N, L605, high tensile stainless steel, precipitation hardenable stainless steel and Elgiloy.

8. The catheter of claim 1 wherein the elongate shaft is comprised of a material selected from the group consisting of high density polyethylene, low density polyethylene, a blend of high density and low density polyethylene and flouropolymer.

9. The catheter of claim 1 further comprising an exit tube having an inner lumen disposed between and in fluid communication with a distal port and a proximal port and having a distal end and a proximal end with the distal end disposed through the intermediate port and into the inner lumen so as to guide a proximal end of a guidewire being proximally advanced within the inner lumen out of the intermediate port.

10. The catheter of claim 1 further comprising a radiopaque marker disposed within a distal end of the inner lumen.

11. A method of exchanging a first guidewire disposed within a patient with a second guidewire comprising:

a) providing a catheter comprising:
an elongate shaft having a proximal end, a distal end with a low profile, an inner lumen extending therein from a proximal port at the proximal end to a distal port at the distal end, an intermediate port disposed between the proximal and distal port, which is in fluid communication with the inner lumen and which is a short distance away from the low profile distal end of the shaft, a longitudinal slit in an outer wall of the inner lumen extending distally from the proximal end, a sidearm disposed on the proximal end of the elongated shaft having a sidearm lumen extending longitudinally therein in fluid communication with the inner lumen of the elongate shaft and having a slit that is aligned with the longitudinal slit of the elongate shaft and a longitudinal support member secured to the elongate shaft;

b) inserting a proximal end of the first guidewire into the distal port of the inner lumen of the catheter;

c) advancing the catheter distally over the first guidewire until the proximal end of the first guidewire exits the intermediate port and the distal end of the catheter is in a desired location;

d) withdrawing the first guidewire proximally out of the patient and out of the inner lumen of the catheter;

e) inserting a distal end of the second guidewire through the sidearm lumen and into the proximal port of the inner lumen of the catheter and distally advancing the second guidewire to a desired location with the patient;

f) pulling a proximal end of the second guidwire laterally through the slit in the sidearm lumen and inner lumen of the elongate shaft while pulling the catheter out of the patient in a proximal direction until the distal end of the catheter can be slid off the proximal end of the second guidewire while the axial position of the second guidewire is maintained.

12. The method of claim 11 including an exit tube in the intermediate port and inserting the proximal end of the first guidewire into a distal end of the exit tube while advancing the catheter distally over the first guidewire to facilitate discharge of the proximal end of the first guidewire from the intermediate port.

13. The method of claim 11 wherein the catheter is used to support the distal end of the guidewire in accessing and crossing a lesion in the desired location prior to withdrawal of the first guidewire.

14. A catheter, comprising:
an elongated shaft having
a) a proximal end,
b) a distal end,
c) a first inner lumen having a distal port at the distal end of the shaft and an intermediate port at a short distance proximal to the distal end of the shaft and distal of a proximal end of the shaft,
d) a second inner lumen with an unobstructed distal port at the distal end of the shaft and a proximal port at the proximal end of the shaft,
e) a longitudinal slit in a wall of the second inner lumen extending distally from the proximal end of the elongated shaft; and
f) a longitudinal support member secured to the elongated shaft for axial support to the catheter.

15. The catheter of claim 14 wherein the longitudinal slit extends from the proximal port to a distal extremity of the longitudinal slit at a point about 30 to about 50 cm proximal of the distal end of the elongate shaft.

16. The catheter of claim 14 further comprising a side arm disposed on the proximal end of the elongated shaft having a sidearm lumen extending longitudinally therein and having a slit in a wall of the sidearm lumen that is aligned with the longitudinal slit of the elongate shaft.

17. The catheter of claim 14 wherein the distance from the distal end of the elongate shaft to the intermediate port is about 25 to about 45 cm.

18. The catheter of claim 14 wherein the longitudinal support member further comprises a proximal section and a distal section and the distal section has at least one distally tapering segment which tapers distally to a reduced transverse cross section.

19. The catheter of claim 18 wherein the distal section comprises a first distally tapering segment disposed proximal to a second distally tapering segment and a first constant diameter segment axially disposed between the two distally tapering segments and a second constant diameter segment disposed axially distal of the second distally tapering segment.

20. The catheter of claim 14 wherein the longitudinal support member comprises a material selected from the group consisting of stainless steel, NiTi, MP35N, L605, high tensile stainless steel, precipitation hardenable stainless steel and Elgiloy.

21. The catheter of claim 14 wherein the elongate shaft is comprised of a material selected from the group consisting of high density polyethylene, low density polyethylene, a blend of high density and low density polyethylene and flouropolymer.

22. The catheter of claim 14 further comprising an exit tube having a proximal end, a distal end, and an inner lumen disposed between and in fluid communication with a distal port at the distal end of the exit tube and a proximal port at the proximal end of the exit tube with the distal end of the exit tube disposed through the intermediate port and into the first inner lumen so as to guide a proximal end of a guidewire being proximally advanced within the inner lumen out of the intermediate port.

23. A method of exchanging a first guidewire disposed at a treatment site within a patient with a second guidewire comprising:
   a) providing a catheter comprising:
      an elongate shaft having a proximal end, a distal end, a first inner lumen with a distal port at the distal end of the shaft and an intermediate port at a position proximal of the distal end of the shaft and distal of the proximal end of the shaft, a second inner lumen with an unobstructed distal port at the distal end of the shaft and a proximal port at the proximal end of the shaft, and a longitudinal slit in a wall of the second inner lumen extending distally from the proximal end of the elongate shaft; and
      a longitudinal support member secured to the elongate shaft;
   b) inserting a proximal end of the first guidewire into the distal port of the first inner lumen;
   c) advancing the catheter distally over the first guidewire until the proximal end of the first guidewire exits the intermediate port and the distal end of the catheter is in a desired location;
   d) inserting a distal end of the second guidewire into the proximal port of the second inner lumen of the shaft and distally advancing the second guidewire to said treatment site within the patient;
   e) withdrawing the first guidewire proximally out of the patient and out of the first inner lumen of the exchange catheter;
   f) pulling the proximal end of the second guidewire laterally through the longitudinal slit in the second inner lumen of the elongate shaft while pulling the catheter out of the patient in a proximal direction until the distal end of the elongate shaft can be slid off the proximal end of the second guidewire while the axial position of the second guidewire is maintained.

24. The method of claim 23 wherein the catheter further comprises an exit tube disposed within the intermediate port and advancing the catheter distally over the first guidewire until the proximal end of the first guidewire engages a port in a distal end of the exit tube thereby facilitating ejection of the proximal end of the guidewire from the intermediate port.

25. The method of claim 23 wherein the catheter is used to support the distal end of the first guidewire in accessing and crossing a lesion in the desired location prior to inserting the distal end of the second guidewire into the proximal port of the second inner lumen.

* * * * *